(12) United States Patent
Roberts et al.

US007078496B2

(10) Patent No.: US 7,078,496 B2
(45) Date of Patent: Jul. 18, 2006

(54) THIOESTER-TERMINATED WATER SOLUBLE POLYMERS AND METHOD OF MODIFYING THE N-TERMINUS OF A POLYPEPTIDE THEREWITH

(75) Inventors: Michael J. Roberts, Williamsburg, VA (US); Zhihao Fang, Madison, AL (US)

(73) Assignee: Nektar Therapeutics AL, Corporation, Huntsville, AL (US)

( * ) Notice: Subject to any disclaimer, the term of this patent is extended or adjusted under 35 U.S.C. 154(b) by 282 days.

(21) Appl. No.: 10/269,028

(22) Filed: Oct. 9, 2002

(65) Prior Publication Data

US 2003/0158333 A1      Aug. 21, 2003

Related U.S. Application Data

(63) Continuation-in-part of application No. 09/973,318, filed on Oct. 9, 2001, now Pat. No. 6,908,963.

(51) Int. Cl.
    C07K 17/02    (2006.01)
    C07K 17/06    (2006.01)
    C07K 17/08    (2006.01)
    C08G 63/50    (2006.01)
(52) U.S. Cl. .................... 530/402; 530/404; 530/408; 514/2; 514/12; 525/54.1; 525/54.2; 525/398; 525/400; 525/437; 525/535; 525/539
(58) Field of Classification Search ............. 530/402, 530/404, 408; 514/2; 515/12; 525/54.1, 525/54.2, 398, 399, 400, 437, 535, 539
See application file for complete search history.

(56) References Cited

U.S. PATENT DOCUMENTS

| | | | |
|---|---|---|---|
| 4,670,417 A | 6/1987 | Iwasaki et al. | |
| 4,904,584 A | 2/1990 | Shaw | |
| 5,206,344 A | 4/1993 | Katre et al. | |
| 5,252,714 A | 10/1993 | Harris et al. | |
| 5,614,549 A | 3/1997 | Greenwald et al. | |
| 5,766,897 A | 6/1998 | Braxton | |
| 5,824,784 A | 10/1998 | Kinstler et al. | |
| 5,932,462 A | 8/1999 | Harris et al. | |
| 5,985,265 A | 11/1999 | Kinstler et al. | |
| 6,010,999 A * | 1/2000 | Daley et al. ............... | 514/2 |
| 6,057,292 A | 5/2000 | Cunningham et al. | |
| 6,184,344 B1 | 2/2001 | Kent et al. | |
| 6,251,382 B1 | 6/2001 | Greenwald et al. | |

FOREIGN PATENT DOCUMENTS

| | | |
|---|---|---|
| WO | WO 96/41813 | 12/1996 |
| WO | WO 98/35026 | 8/1998 |
| WO | WO 99/03887 | 1/1999 |
| WO | WO 99/24472 | 5/1999 |
| WO | WO 99/45026 | 9/1999 |
| WO | WO 99/67291 | 12/1999 |

OTHER PUBLICATIONS

Ayers, et al., "Introduction of Unnatural Amino Acids into Proteins Using Expressed Protein Ligation", *Biopolymers (Peptide Science)*, 1999, pp. 343-354, vol. 51.
Clippingdale, et al., "Peptide Thioester Preparation by Fmoc Solid Phase Peptide Synthesis for Use in Native Chemical Ligation", *J. Peptide Sci.*, 2000, pp. 225-234, vol. 6.
Dawson, et al., "Synthesis of Proteins by Native Chemical Ligation", *Science*, 1994, pp. 776-779, vol. 266.
Hackeng, et al., "Protein Synthesis by Native Chemical Ligation: Expanded Scope by Using Straightforward Methodology", *Proc. Natl. Acad. Sci. USA*, 1999, pp. 10068-10073, vol. 96.
Hansen, et al., "Attachment of Antibodies to Sterically Stabilized Liposomes: Evaluation, Comparison and Optimization of Coupling Procedures", *Biochimica et Biophysica Acta 1239*, 1995, pp. 133-144.
Hershfield et al., "Use of Site-Directed Mutagenesis to Enhance the Epitope-Shielding Effect of Covalent Modification of Proteins with Polyethylene Glycol", *Proc. Natl. Acad. Sci. USA*, 1991, pp. 7185-7189, vol. 88.
Tam, et al., "Peptide Synthesis Using Unprotected Peptides Through orthogonal Coupling Methods", *Proc. Natl. Acad. Sci. USA*, 1995, pp. 12485-12489, vol. 92.
Tam, et al., "Orthogonal Ligation Strategies for Peptide and Protein", *Biopolymers (Peptide Science)*, 1999, pp. 311-332, vol. 51.
Zalipsky et al., "Facile Synthesis of α-Hydroxy-ω-Carboxymethylpolyetheylene Oxide", *Journal of Bioactive and Compatible Polymers*, 1990, pp. 227-231, vol. 5.
Zalipsky, "Synthesis of an End-Group Functionalized Polyethylene Glycol-Lipid Conjugate for Preparation of Polymer-Grafted Liposomes", *Bioconjugate Chem.*, 1993, pp. 296-299, vol. 4.
Zalipsky et al., "Hydrazide Derivatives of Poly(ethylene glycol) and Their Bioconjugates", *American Chemical Society*, 1997, pp. 318-340.

* cited by examiner

*Primary Examiner*—Irina Zemel
(74) *Attorney, Agent, or Firm*—Alston & Bird LLP

(57) ABSTRACT

The invention provides reagents and methods for conjugating a polymer specifically to the α-amine of a polypeptide. The invention provides monofunctional, bifunctional, and multifunctional PEGs and related polymers having a terminal thioester moiety capable of specifically conjugating to the α-amine of a polypeptide having a cysteine or histidine residue at the N-terminus. The invention provides reactive thioester-terminated PEG polymers that have suitable reactivity with an N-terminal cysteine or histidine residue of a polypeptide to produce an amide bond between the PEG molecule and the polypeptide.

43 Claims, No Drawings

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Polypeptide having 20 amino acid residues and an
      N-terminal cysteine.

<400> SEQUENCE: 1

Cys Arg Ala Ser Lys Ser Val Ser Ser Ser Gly Tyr Ser Tyr Met His
1               5                   10                  15

Trp Tyr Gln Gln
            20
```

THIOESTER-TERMINATED WATER SOLUBLE POLYMERS AND METHOD OF MODIFYING THE N-TERMINUS OF A POLYPEPTIDE THEREWITH

CROSS-REFERENCE TO RELATED APPLICATIONS

This application is a continuation-in-part of U.S. application Ser. No. 09/973,318, filed Oct. 9, 2001, now U.S. Pat. No. 6,908,963 which is incorporated by reference herein in its entirety.

FIELD OF THE INVENTION

The invention relates to water soluble polymers useful for selectively conjugating to the N-terminus of a polypeptide.

BACKGROUND OF THE INVENTION

Covalent attachment of the hydrophilic polymer poly (ethylene glycol), abbreviated PEG, also known as poly (ethylene oxide), abbreviated PEO, to molecules and surfaces is of considerable utility in biotechnology and medicine. PEG is a polymer having the beneficial properties of solubility in water and in many organic solvents, lack of toxicity, and lack of immunogenicity. One use of PEG is to covalently attach the polymer to water-insoluble molecules to improve the solubility of the resulting PEG-molecule conjugate. For example, it has been shown that the water-insoluble drug paclitaxel, when coupled to PEG, becomes water-soluble. Greenwald, et al., *J. Org. Chem.*, 60:331–336 (1995). PEG has also been used increasingly in the modification of polypeptide and protein therapeutics.

The use of polypeptides, including proteins, for therapeutic applications has expanded in recent years mainly due to both improved methods for recombinant expression of human polypeptides from various expression systems and improved methods of delivery in vivo. Many of the drawbacks associated with polypeptide therapeutics, including short circulating half-life, immunogenicity and proteolytic degradation, have been improved by various approaches including gene therapy, epitope mutations by directed or shuffling mutagenesis, shielding of the epitope regions by natural or synthetic polymers, fusion proteins, and incorporation of the polypeptide into drug delivery vehicles for protection and slow release.

Polymer modification of proteins, such as covalent attachment of poly(ethylene glycol), has gained popularity as a method to improve the pharmacological and biological properties of therapeutically useful proteins. For example, certain poly(ethylene glycol) conjugated proteins have been shown to have significantly enhanced plasma half-life, reduced antigenicity and immunogenicity, increased solubility and decreased proteolytic degradation when compared to their non-pegylated counterparts. Factors that affect the foregoing properties are numerous and include the nature of the protein itself, the number of poly(ethylene glycol) or other polymer chains attached to the protein, the molecular weight and structure of the polymer chains attached to the protein, the chemistries (i.e., the particular linkers) used to attach the polymer to the protein, and the location of the polymer modified-sites on the protein.

To couple PEG to a molecule, such as a protein, it is often necessary to "activate" the PEG by preparing a derivative of the PEG having a functional group at a terminus thereof. The functional group is chosen based on the type of available reactive group on the molecule that will be coupled to the PEG. For example, the functional group could be chosen to react with an amino group on a protein in order to form a PEG-protein conjugate.

A variety of methods have been developed to non-specifically or randomly attach poly(ethylene glycol) to proteins. Most commonly, electrophilically-activated poly(ethylene glycol) is reacted with nucleophilic side chains found of proteins. Attaching an activated poly(ethylene glycol) to the α-amine and ε-amine groups found on lysine residues and at the N-terminus results in a mixture of conjugate products as described in U.S. Pat. No. 6,057,292. For example, the conjugate may consist of a population of conjugated proteins having varying numbers of poly(ethylene glycol) molecules attached to the protein molecule ("PEGmers"), ranging from zero to the number of α- and ε-amine groups in the protein. Often, random pegylation approaches are undesirable, due to variations in the ratios of PEG-mer products produced, and the desire, in certain cases, for a single, discrete PEG-protein conjugate product. For a protein molecule that has been singly modified by employing a non-site specific pegylation methodology, the poly (ethylene glycol) moiety may be attached at any one of a number of different amine sites. Additionally, this type of non-specific PEGylation can result in partial or complete loss of the therapeutic utility of the conjugated protein, particularly for conjugates having more than one PEG attached to the protein.

Several methods for site-directed or selective attachment of PEG have been described. For example, WO 99/45026 suggests chemical modification of a N-terminal serine residue to form an aldehyde functionality suitable for reaction with a polymer terminated with a hydrazide or semicarbazide functionality. U.S. Pat. Nos. 5,824,784 and 5,985,265 suggest reacting a polymer bearing a carbonyl group with the amino terminus of a protein under reducing alkylation conditions and at a pH that promotes selective attack at the N-terminus. WO 99/03887 and U.S. Pat. Nos. 5,206,344 and 5,766,897 relate to the site-directed PEGylation of cysteine residues that have been engineered into the amino acid sequence of proteins (cysteine-added variants). While these methods offer some advantages over non-specific attachment, there is a continuing unmet need for improved methods and reagents for providing site-specific polymer-conjugated proteins that do not require chemical modification of the polypeptide or careful control of certain reaction conditions, such as pH. Additionally, due to the high desirability for modifying a protein at its reactive amino-functionalities, there is a need for improved polymer reagents that react selectively with a specific protein amino group, such as the N-terminal amino group, for preparing protein-polymer conjugates that are not a mixture of PEG-polymer PEGmers but rather have PEG attached to a single, identified site on the protein.

SUMMARY OF THE INVENTION

This invention provides reagents and methods for conjugating polymers specifically to the α-amino group of a polypeptide. The invention provides monofunctional, bifunctional, and multifunctional PEGs and related polymers having a thioester (also referred to as a thiol ester) moiety capable of specifically conjugating to the a-amine of a polypeptide having a cysteine or histidine at the N-terminus. Thus, the invention provides reactive thioester-terminated PEG polymers effective to react site-specifically with an N-terminal cysteine or histidine residue of a polypeptide to produce an amide-linked PEG-polypeptide conjugate.

In one aspect, the invention provides a thioester-terminated reactive polymer comprising a water soluble and non-peptidic polymer backbone having at least one terminus bonded to the structure:

$$L-(Z)_a-(CH)_m-\overset{X}{\underset{}{}}\overset{Y}{\underset{\|}{C}}-Q \qquad \text{Formula I}$$

wherein,

L is the point of bonding to a water soluble and non-peptidic polymer backbone;

Z is a hydrolytically stable linkage or a hydrolytically unstable linkage, such as O, S, —NHCO—, —CONH—, —O$_2$C—, —NHCO$_2$—, or —O$_2$CNH—;

a is 0 or 1;

each X is independently selected from H and alkyl, such as C1–C6 alkyl;

m is from 0 to about 12, preferably 1 to about 4;

Y is a heteroatom, preferably O or S; and

Q is a sulfur-containing leaving group preferably having the formula —S—R$_1$, wherein R$_1$ is hydrogen, alkyl, substituted alkyl, cycloalkyl, substituted cycloalkyl, aryl, substituted aryl, heteroaryl, substituted heteroaryl, heterocycle, or substituted heterocycle.

The reactive polymer may be monofunctional (e.g., mPEG), bifunctional, or multifunctional. The polymer backbone is preferably a poly(alkylene glycol), such as poly (ethylene glycol), poly(propylene glycol), or a copolymer of ethylene glycol and propylene glycol. Examples of other suitable polymer backbones include poly(oxyethylated polyol), poly(olefinic alcohol), poly(vinylpyrrolidone), poly (α-hydroxy acid), poly(vinyl alcohol), polyphosphazene, polyoxazoline, poly(N-acryloylmorpholine), polyacrylate, polyacrylamides, polysaccharides, and copolymers, terpolymers, and mixtures thereof.

In another aspect, the invention provides a polymer conjugate of a polypeptide having a cysteine or histidine molecule at the N-terminus, the polymer conjugate comprising a water soluble and non-peptidic polymer backbone having at least one terminus bonded to the structure:

$$L-(Z)_a-(CH)_m-\overset{X}{\underset{}{}}\overset{Y}{\underset{\|}{C}}-\underset{H}{N}-\overset{W}{\underset{H}{C}}-\text{POLYPEPTIDE}$$

wherein

L, Z, m, Y, X and a are as defined above,

W is —CH$_2$SH or

[imidazole structure: —CH$_2$— attached to imidazole ring with N, NH]

and

POLYPEPTIDE is a polypeptide molecule, where —NH—C(W)H— represents the N-terminal cysteine or histidine residue (absent one hydrogen atom) of the polypeptide. Examples of polypeptides that can be conjugated to the thioester-terminated polymers of the invention include, but are not limited to, proteins, protein-ligands, enzymes, cytokines, hematopoietins, growth factors, hormones, antigens, antibodies, antibody fragments, receptors, and protein fragments.

In yet another aspect, a method of conjugating a polymer derivative to a polypeptide having a cysteine or histidine molecule at the N-terminus is also provided. The method comprises providing both a polypeptide having a cysteine or histidine molecule at the N-terminus and a thioester-terminated polymer as described above. The polypeptide is reacted with the thioester-terminated polymer to form, in a site specific manner, a conjugate having an amide linkage between the residue of the N-terminal histidine or cysteine molecule and the reactive polymer. The thioester-terminated polymer selectively attaches to the N-terminal amine group of the histidine or cysteine residue of the polypeptide without reacting with free amine groups at other positions within the polypeptide.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The following terms as used herein have the meanings indicated.

As used in the specification, and in the appended claims, the singular forms "a", "an", "the", include plural referents unless the context clearly dictates otherwise.

The terms "functional group", "active moiety", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group. As used herein, the term "functional group" includes protected functional groups.

The term "protected functional group" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *PROTECTIVE GROUPS IN ORGANIC SYNTHESIS*, 3rd ed., John Wiley & Sons, New York, N.Y. (1999).

The term "linkage" or "linker" (L) is used herein to refer to an atom or a collection of atoms used to link, preferably by one or more covalent bonds, interconnecting moieties such two polymer segments or a terminus of a polymer and a reactive functional group present on a bioactive agent, such as a polypeptide. A linker of the invention may be hydrolytically stable or may include a physiologically hydrolyzable or enzymatically degradable linkage A "physiologically hydrolyzable" or "hydrolytically degradable" bond is a weak bond that reacts with water (i.e., is hydrolyzed) under physiological conditions. Preferred are bonds that have a hydrolysis half life at pH 8, 25° C. of less than about 30 minutes. The tendency of a bond to hydrolyze in water will depend not only on the general type of linkage connecting two central atoms but also on the substituents attached to these central atoms. Appropriate hydrolytically unstable or degradable linkages include but are not limited to carboxylate ester, phosphate ester, anhydrides, acetals, ketals, acyloxyalkyl ether, imines, orthoesters, peptides and oligonucleotides.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1–2% per day under physiological conditions. Hydrolysis rates of representative chemical bonds can be found in most standard chemistry textbooks.

An "enzymatically unstable" or degradable linkage is a linkage that can be degraded by one or more enzymes.

The term "polymer backbone" refers to the covalently bonded chain of repeating monomer units that form the polymer. For example, the polymer backbone of PEG is —CH$_2$CH$_2$O—(CH$_2$CH$_2$O)$_n$—CH$_2$CH$_2$— where n typically ranges from about 2 to about 4000. As would be understood, the polymer backbone may be covalently attached to terminal functional groups or pendant functionalized side chains spaced along the polymer backbone.

The term "reactive polymer" refers to a polymer bearing at least one reactive functional group.

Unless otherwise noted, molecular weight is expressed herein as number average molecular weight ($M_n$), which is defined as

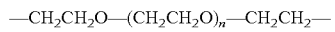

wherein Ni is the number of polymer molecules (or the number of moles of those molecules) having molecular weight Mi.

The term "alkyl" refers to hydrocarbon chains typically ranging from about 1 to about 12 carbon atoms in length, preferably 1 to about 6 atoms, and includes straight and branched chains. The hydrocarbon chains may be saturated or unsaturated.

"Cycloalkyl" refers to a saturated or unsaturated cyclic hydrocarbon chain, including bridged, fused, or spiro cyclic compounds, preferably comprising 3 to about 12 carbon atoms, more preferably 3 to about 8.

The term "substituted alkyl" or "substituted cycloalkyl" refers to an alkyl or cycloalkyl group substituted with one or more non-interfering substituents, such as, but not limited to, C3–C8 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably C1–C6 alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents. For substitutions on a phenyl ring, the substituents may be in any orientation (i.e., ortho, meta or para).

"Heteroaryl" is an aryl group containing from one to four heteroatoms, preferably N, O, or S, or a combination thereof, which heteroaryl group is optionally substituted at carbon or nitrogen atom(s) with C1–6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

"Substituted heteroaryl" is heteroaryl having one or more non-interfering groups as substituents.

"Heterocycle" or "heterocyclic" means one or more rings of 5–12 atoms, preferably 5–7 atoms, with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents are those groups that, when present in a molecule, are typically non-reactive with other functional groups contained within the molecule.

Suitable non-interfering substituents or radicals include, but are not limited to, halo, C1–C10 alkyl, C2–C10 alkenyl, C2–C10 alkynyl, C1–C10 alkoxy, C7–C12 aralkyl, C7–C12 alkaryl, C3–C10 cycloalkyl, C3–C10 cycloalkenyl, phenyl, substituted phenyl, toluoyl, xylenyl, biphenyl, C2–C12 alkoxyalkyl, C7–C12 alkoxyaryl, C7–C12 aryloxyalkyl, C6–C12 oxyaryl, C1–C6 alkylsulfinyl, C1–C10 alkylsulfonyl, —(CH$_2$)$_m$—O—(C1–C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1–C10 alkyl), —C(O)—(C1–C10 alkyl), C2–C10 thioalkyl, —C(O)O—(C1–C10 alkyl), —OH, —SO$_2$, =S, —COOH, —NR, carbonyl, —C(O)—(C1–C10 alkyl)—CF$_3$, —C(O)—CF$_3$, —C(O)NR$_2$, —(C1–C10 alkyl)—S—(C6–C12 aryl), —C(O) —(C6–C 12 aryl), —(CH$_2$)$_m$O—(C1–C10 alkyl) wherein each m is from 1 to 8, —C(O)NR, —C(S)NR, —SO$_2$NR, —NRC(O)NR, —NRC(S)NR, salts thereof, and the like. Each R as used herein is H, alkyl or substituted alkyl, aryl or substituted aryl, aralkyl, or alkaryl.

"Heteroatom" means any non-carbon atom in a hydrocarbon analog compound. Examples include oxygen, sulfur, nitrogen, phosphorus, arsenic, silicon, selenium, tellurium, tin, and boron.

The term "drug", "biologically active molecule", "biologically active moiety" or "biologically active agent", when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like. "Polyolefinic alcohol" refers to a polymer comprising a polyolefin backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

"Polypeptide" or "poly(amino acid)" refers to any molecule comprising a series of amino acid residues, typically at least about 10–20 residues, linked through amide linkages (also referred to as peptide linkages) along the alpha carbon backbone. While in some cases the terms may be used synonymously herein, a polypeptide is a peptide typically having a molecular weight up to about 10,000 Da, while peptides having a molecular weight above that are commonly referred to as proteins. Modifications of the peptide side chains may be present, along with glycosylations, hydroxylations, and the like. Additionally, other non-peptidic molecules, including lipids and small drug molecules, may be attached to the polypeptide. The polypeptide may comprise any combination or sequence of amino acid residues. The polymers of the invention are suitable for covalent attachment to both polypeptides and proteins.

"Amino acid" refers to organic acids containing both a basic amine group and an acidic carboxyl group. The term encompasses essential and non-essential amino acids and both naturally occurring and synthetic or modified amino acids. The most common amino acids are listed herein by either their full name or by the three letter or single letter abbreviations: Glycine (Gly, G), Alanine (Ala, A), Valine (Val, V), Leucine (Leu, L), Isoleucine (Ile, I), Methionine (Met, M), Proline (Pro, P), Phenylalanine (Phe, F), Tryptophan (Trp, W), Serine (Ser, S), Threonine (Thr, T), Asparagine (Asn, N), Glutamine (Gln, Q), Tyrosine, (Tyr, Y), Cysteine (Cys, C), Lysine (Lys, K), Arginine (Arg, R), Histidine (His, H), Aspartic Acid (Asp, D), and Glutamic acid (Glu, E).

By "residue" is meant the portion of a molecule remaining after reaction with one or more molecules. For example, an amino acid residue in a polypeptide chain is the portion of an amino acid remaining after forming peptide linkages with adjacent amino acid residues. "Oligomer" refers to short monomer chains comprising 2 to about 10 monomer units, preferably 2 to about 5 monomer units.

The term "conjugate" is intended to refer to the entity formed as a result of covalent attachment of a molecule, such as a biologically active molecule, to a reactive polymer molecule, preferably poly(ethylene glycol).

The term "leaving group" refers to an atom or collection of atoms covalently attached to an atom (such as a carbon atom) and that can be readily displaced from the atom, taking with it its bonding electrons. Typically, the leaving group is an anion or a neutral molecule. The better the leaving group, the more likely it is to depart from the atom to which it is bonded. Representative good leaving groups are those that are the conjugate base of a strong acid.

"Multifunctional" in the context of a polymer of the invention means a polymer having 3 or more functional groups attached thereto, where the functional groups may be the same or different. Multifunctional polymers of the invention will typically comprise from about 3–100 functional groups, or from 3–50 functional groups, or from 3–25 functional groups, or from 3–15 functional groups, or from 3 to 10 functional groups, or will contain 3, 4, 5, 6, 7, 8, 9 or 10 functional groups attached to the polymer backbone.

II. Thioester Polymers

In one aspect, the present invention provides thioester-terminated water soluble polymers capable of selectively reacting with the N-terminal amino group of a polypeptide to form a polymer-polypeptide conjugate comprising a single water soluble polymer chain attached at the N-terminus. Such a polymer-polypeptide conjugate is referred to herein as mono-substituted (meaning a polymer chain is substituted at only one site of the polypeptide). Modification of a polypeptide at only a single site is beneficial because the likelihood of a significant reduction in bioactivity due to the presence of the polymer chain is lessened as compared to indiscriminate or random polymer attachment at various and multiple sites along the polypeptide chain. Moreover, the polymers and method provided herein for forming site-specific conjugates provide an additional advantage over commonly employed prior art methods since multiple protection/deprotection steps to prevent reaction of the polymer with other reactive groups/positions contained within the polypeptide are unnecessary. Additionally, such site selective modification eliminates the need for additional conjugate purification steps to isolate particular (e.g., monopegylated) conjugate species. Thus, use of the thioester polymers of the invention can offer the above advantages while additionally providing the beneficial properties of water-soluble polymer attachment, such as increased water solubility, enhanced plasma half-life, and decrease in proteolytic degradation as compared to an unmodified polypeptide.

As explained in greater detail below, the thioester-terminated polymers of the invention selectively react with an N-terminal cysteine or histidine residue of a polypeptide. Without being bound by theory, the reaction involves nucleophilic attack of the thioester group by either the thiol side chain of a cysteine residue or the imidazole side chain of a histidine residue to form a thioester intermediate. The thioester intermediate then undergoes a rapid rearrangement that results in transfer of the acyl group of the polymer to the terminal amine group of the polypeptide, thereby producing a peptide bond between the polymer and the N-terminus of the polypeptide. As would be understood, since only an N-terminal cysteine or histidine residue would provide the side chain necessary for the initial reaction step (e.g., attack on the polymer thioester carbonyl carbon by a reactive thiol group of a protein having an N-terminal cysteine), the polymers of the invention will, via a molecular rearrangement, specifically attach to the N-terminal amine without reacting with any other side chain amine groups that may be present in the polypeptide molecule. The present invention is particularly useful for site-specific PEG attachment of polypeptides containing more than one free cysteine or histidine, even in the unfolded state. The polymers and conjugation methods of the present invention can be used to assist insoluble polypeptides that are in the unfolded state to refold to their native conformation.

The thioester-terminated polymers of the invention comprise a polymer backbone attached to a thioester group with an optional intervening linkage between the terminus of the polymer backbone and the thioester group. The thioester-terminated polymers of the invention have the structure:

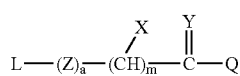

Formula I wherein,

L is the point of bonding to a water soluble and non-peptidic polymer backbone;

Z is a hydrolytically stable linkage or a hydrolytically unstable linkage, such as O, S, —NHCO—, —CONH—, —O$_2$C—, —NHCO$_2$—, or —O$_2$CNH—;

m is from 0 to about 12, preferably 1 to about 4;

each X is independently selected from H and alkyl, such as C1–C6 alkyl;

a is 0 or 1;

Y is a heteroatom, preferably O or S; and

Q is a sulfur-containing leaving group preferably having the formula —S—R$_1$, wherein R$_1$ is hydrogen, alkyl, substituted alkyl, cycloalkyl, substituted cycloalkyl, aryl, substituted aryl, heteroaryl, substituted heteroaryl, heterocycle, or substituted heterocycle.

A. Polymer Backbone

In general, the water soluble and non-peptidic polymer backbone should be non-toxic and biocompatible, meaning that the polymer is capable of coexistence with living tissues or organisms without causing harm. When referring to a thioester-terminated polymer backbone herein, it is to be understood that the polymer backbone can be any of a number of water soluble and non-peptidic polymers, such as those described below. Preferably, poly(ethylene glycol) (PEG) is the polymer backbone. The term PEG includes poly(ethylene glycol) in any of a number of geometries or forms, including linear forms (e.g., alkoxy PEG or bifunctional PEG), branched or multi-arm forms (e.g., forked PEG or PEG attached to a polyol core), pendant PEG, or PEG with degradable linkages therein, to be more fully described below.

In its simplest form, PEG has the formula

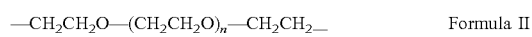

Formula II wherein n is from about 10 to about 4000, typically from about 20 to about 2000. Although the number average molecular weight of the PEG polymer backbone can vary, PEGs having a number average molecular weight of from about 100 Da to about 100,000 Da, preferably about 5,000 Da to about 60,000 Da are particularly useful. For example, PEG polymers having a molecular weight of about 100 Da, about 200 Da, about 300 Da, about 500 Da, about 800 Da, about 1,000 Da, about 2,000 Da, about 3,000 Da, about 4,000 Da, about 5,000 Da, about 10,000 Da, about 15,000, about 20,000, about 30,000 and about 40,000 are useful in the present invention.

End-capped polymers, meaning polymers having at least one terminus capped with a relatively inert group (e.g., an alkoxy group), can also be used as the polymer backbone of the invention. For example, methoxy-PEG-OH, or mPEG in brief, is a form of PEG wherein one terminus of the polymer backbone is bonded to a methoxy group, while the other terminus is a hydroxyl group that is subject to ready chemical modification. The structure of mPEG is given below.

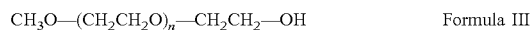

Formula III wherein n is as described above.

Monomethoxy-terminated PEG molecules having a number average molecular weight of about 100 to about 100,000 Da, more preferably about 2,000 to about 60,000 Da, are typically preferred for conjugating to proteins. Use of a monofunctional polymer such as mPEG prevents cross-linking of the protein that often occurs when bifunctional or multifunctional reagents are used. In the present invention, mPEG-thioester can be used to produce a single PEG molecule attached to a single protein molecule. However, in an alternate embodiment, utilizing a homobifunctional PEG-thioester in appropriate proportions will result in a conjugate having two protein molecules attached to a single PEG molecule, even in the event the protein contains multiple free cysteine residues. Due to the manner in which the PEG derivative is believed to react (i.e. initially linking through the available thiol group of the N-terminal cysteine residue and then rearranging to form the amide linkage), it is not possible for the thioester polymer derivatives of the invention to give a cross-linked protein because other free cysteine residues will not have both an available thiol group and an available amine group. Thus, another advantage of the present invention is the ability to use polymers with multiple functional groups of the type described herein without undesirable crosslinking with the polypeptide.

Multi-armed or branched PEG molecules, such as those described in U.S. Pat. No. 5,932,462, which is incorporated by reference herein in its entirety, can also be used as the PEG polymer. For example, the PEG polymer backbone can have the structure:

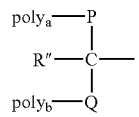

Formula IV wherein:

$poly_a$ and $poly_b$ are PEG backbones, such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

The PEG polymer may alternatively comprise a forked PEG. An example of a forked PEG is represented by PEG-YCHZ$_2$, where Y is a linking group and Z is an activated terminal group, such as the aldehyde group of the present invention, linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, an alkyl chain, ether linkage, ester linkage, amide linkage, or combinations thereof.

The PEG polymer may comprise a pendant PEG molecule having reactive groups, such as carboxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more weak or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

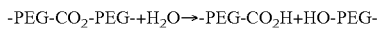

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

Many other polymers are also suitable for the invention. Any of a variety of monofunctional, bifunctional or multifunctional polymer backbones that are non-peptidic and water-soluble could be used in the present invention. The polymer backbone can be linear, or may be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly (vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof.

B. Linkage Between Polymer Backbone and Thioester

The intervening linkage between the terminus of the polymer backbone and the thioester group is the residue of the functional group on the polymer backbone that couples the polymer backbone to the terminal thioester group. Thus, as would be understood, the structure of the linkage will vary depending on the structure of the functional group of the polymer backbone. The linkage can comprise a hydrolytically stable linkage, such as amide, urethane, ether, thioether, or urea. Alternatively, the linkage can comprise a hydrolytically unstable linkage, such as carboxylate ester, phosphate ester, orthoester, anhydride, imine, acetal, ketal, oligonucleotide, or peptide. In one embodiment, in addition to the hydrolytically stable or unstable linkage, the linkage between the polymer backbone and the thioester includes an optional alkylene spacer, designated herein as (CHX)$_m$.

As shown above in Formula I, the linkage preferably has the structure:

Formula Ia wherein:

Z is the hydrolytically stable or unstable linkage, such as O, S, —NHCO—, —CONH—, —O$_2$C—, —NHCO$_2$—, or —O$_2$CNH—;

m is from 0 to about 12, preferably 1 to about 4;

each X is independently selected from H and alkyl, such as C1–C6 alkyl; and a is 0 or 1.

The length of the alkylene chain (i.e., the value of in) can vary from 0 to about 12. For example, m can be 0, 1, 2, 3, 4, 5, 6, 7, 8, 9, 10, 11, or 12. Preferably, m is 0, 1, 2, 3, or 4. Each X of the alkylene chain is preferably hydrogen, methyl or ethyl. In a preferred embodiment, a is 1 and Z is a heteroatom, such as O or S.

C. Thioester Functional Group

The thioester functional group is covalently attached to at least one terminus of the water soluble polymer. The thioester group has the structure:

Formula Ib wherein:

Y is a heteroatom, preferably O or S; and

Q is a sulfur-containing electrophilic leaving group preferably having the formula —S—$R_1$, wherein $R_1$ is hydrogen, alkyl, substituted alkyl, cycloalkyl, substituted cycloalkyl, aryl, substituted aryl, heteroaryl, substituted heteroaryl, heterocycle, or substituted heterocycle.

The particular $R_1$ group employed can vary. The $R_1$ group, in conjunction with the sulfur atom, forms an electrophilic leaving group suitable for displacement during nucleophilic attack of the carbonyl carbon by the thiol or imidazole side chain of the N-terminal amino acid residue of a polypeptide. Preferred $R_1$ groups include substituents derived from phenol, nitrophenol, benzoic acid, pyridine, pyridinecarboxylic acid, and nitropyridine. Substituted or unsubstituted pyridinyl is particularly preferred. Examples 1–3 illustrate thioester-terminated PEG polymers bearing a thiopyridinyl leaving group.

D. Exemplary Polymer Structures

An embodiment of a linear polymer of the invention can be structurally represented as shown below:

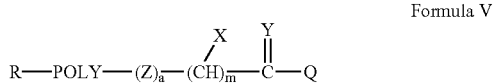

Formula V wherein POLY is a water soluble and non-peptidic polymer backbone, R is a capping group or a functional group, and Z, X, Y, m, a and Q are as defined above. In a preferred embodiment, R is methoxy, POLY is poly(ethylene glycol), a is 1, Z is O, m is 1 to about 3, Y is O, and each X is H or $CH_3$.

The R group can be a relatively inert capping group, such as alkoxy (e.g., methoxy or ethoxy), alkyl, benzyl, aryl, or aryloxy (e.g., benzyloxy). Alternatively, the R group can be a functional group capable of readily reacting with a functional group on a biologically active molecule. Exemplary functional groups include hydroxyl, active ester (e.g. N-hydroxysuccinimidyl ester or 1-benzotriazolyl ester), active carbonate (e.g. N-hydroxysuccinimidyl carbonate and 1-benzotriazolyl carbonate), acetal, aldehyde, aldehyde hydrate, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, or tresylate. Specific examples of terminal functional groups for the polymer backbones of the invention include N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170–181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824, 784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900, 461). All of the above references are incorporated herein by reference.

In a homobifunctional embodiment of Formula V, R is a thioester-containing moiety of formula —$(Z)_a$—$(CXH)_m$—CO—S—$R_1$, wherein Z, a, x, m, and $R_1$ are as defined above.

Some specific examples of linear polymers of the invention are shown below:

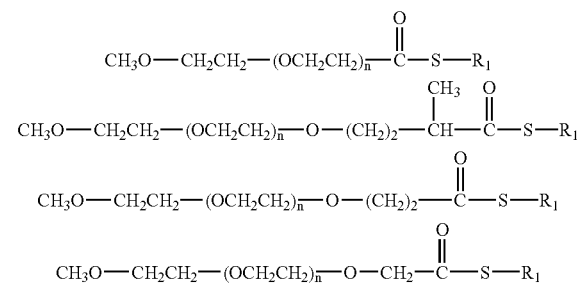

wherein $R_1$ and n are as defined above.

One example of a multi-arm embodiment of the thioester-terminated polymer of the invention has the structure:

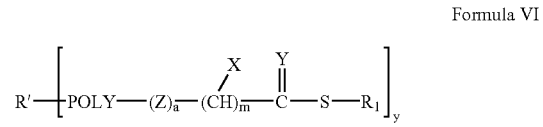

Formula VI wherein each POLY is a water soluble and non-peptidic polymer backbone, R' is a central core molecule, y is from about 3 to about 100, preferably 3 to about 25, and Z, X, Y, m, a and $R_1$ are as defined above. The core moiety, R', is a residue of a molecule selected from the group consisting of polyols, polyamines, and molecules having a combination of alcohol and amine groups. Specific examples of central core molecules include glycerol, glycerol oligomers, pentaerythritol, sorbitol, and lysine.

The central core molecule is preferably a residue of a polyol having at least three hydroxyl groups available for polymer attachment. A "polyol" is a molecule comprising a plurality of available hydroxyl groups. Depending on the desired number of polymer arms, the polyol will typically comprise 3 to about 25 hydroxyl groups. The polyol may include other protected or unprotected functional groups as well without departing from the invention. Although the spacing between hydroxyl groups will vary from polyol to polyol, there are typically 1 to about 20 atoms, such as carbon atoms, between each hydroxyl group, preferably 1 to about 5. Preferred polyols include glycerol, reducing sugars such as sorbitol, pentaerythritol, and glycerol oligomers, such as hexaglycerol. A 21-arm polymer can be synthesized using hydroxypropyl-β-cyclodextrin, which has 21 available hydroxyl groups. The particular polyol chosen will depend on the desired number of hydroxyl groups needed for attachment to the polymer arms.

E. Method of Forming Thioester Polymers

The thioester polymers of the invention may be formed by derivatization of a water-soluble non-peptidic polymer by any of a number of synthetic approaches for forming thioesters known in the art. See, for example, Field, L. *Synthesis*, 1972, 106. For instance, a thioester can be prepared from the corresponding acid chloride-terminated polymer by reaction with a thallium(I) salt of a thiolate (Spessard, G., et al., Organic Synthesis Collection, Vol. 7, 87). For thioester derivatization of a polymer having additional functional groups contained within the molecule, such as hydroxy or other functional groups, alternative approaches such as the following may be employed. For example, a thioester-terminated polymer as described herein can be formed from the corresponding carboxylic acid-terminated polymer by reaction of the acid with a dialkyl or diphenyl phosphorochloridate to form the anhydride, which can then be converted to the corresponding thioester. (Masamune, S., et al., *Can. J. Chem.*, 1975, 53, 3693; Yamada, S., et al., *Chem. Pharm. Bull.* 1977, 25, 2423). In yet another synthetic approach, a thioester-terminated polymer can be prepared by reaction of an imidazolide of a carboxylic acid (prepared by reaction of the corresponding carboxylic acid with N,N-carbonyldiimidazole) with a relatively acidic thiol (Masamune, S., et al., *J. Am. Chem. Soc.*, 1976, 98, 7874). Alternatively, a disulfide and triphenylphosphine can be used to convert a carboxylic acid terminus of a polymer to the corresponding thioester (Mukaiyama, T., et al., *Bull. Chem. Soc. Jpn.*, 1970, 43, 1271). Other methods that can be used to prepare thioesters from carboxylic acids include the use of aryl thiocyanates (Grieco, P., et al., *J. Org. Chem.*, 1978, 43, 1283), thiopyridyl chloroformate (Corey, E. J., et al., *Tetrahedron Lett.*, 1979, 2875), 2-fluoro-N-methylpyridinium tosylate (Watanabe, Y., et al., *Chem. Lett.* 1976, 741), 1-hydroxybenzotrizaole (Horiki, K., *Synth. Commun.* 1977, 7, 251), and boron thiolate (Pelter, A., et al., *J. Chem. Soc., Perkin Trans. 1*, 1977, 1672). Alternatively, a polymer having an O-ester terminus can be converted to the corresponding S-ester by aluminum and boron reagents.

A preferred method of forming the thioester polymers of the invention involves base-catalyzed reaction of a terminal carboxylic acid, or active ester thereof, of a reactive polymer with a thiol compound of formula $R_1$—SH, wherein $R_1$ is as defined above. Preferred reactive polymers bearing a terminal carboxylic acid group include poly(ethylene glycol) terminated with a carboxymethyl, propionic acid, or butanoic acid group. Any other method known in the art for coupling a thioester group to a terminus of a polymer backbone, such as any of those described above, could also be used without departing from the present invention. Exemplary methods of forming thioester-terminated polymers are illustrated in Examples 1–3.

III. Polymer/Polypeptide Conjugates

A. Structure of Polymer/Polypeptide Conjugate

The thioester polymers of the invention selectively react with the α-amine of a polypeptide having a histidine or cysteine molecule at the N-terminus to form an amide linkage between the polymer and the polypeptide. In a preferred embodiment, the polymer-polypeptide conjugate comprises a water soluble and non-peptidic polymer backbone having at least one terminus bonded to the structure:

Formula VII

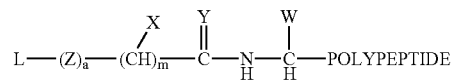

wherein:

L, Z, Y, m, X and a are defined above;

W is —CH$_2$SH or

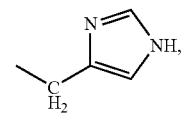

depending on whether the terminal amino acid is cysteine or histidine; and

POLYPEPTIDE is the polypeptide molecule. The polymer backbone can comprise any of the polymer structures discussed above, such as PEG in any of its forms.

The polypeptide can be any polypeptide having an N-terminal cysteine or histidine residue, regardless of whether the N-terminal cysteine or histidine is naturally occurring in the polypeptide or introduced by modification of the polypeptide sequence. The polypeptide molecule is preferably selected from the group consisting of proteins, protein-ligands, enzymes, cytokines, hematopoietins, growth factors, hormones, antigens, antibodies, antibody fragments, receptors, and protein fragments. The following is an illustrative although by no means exhaustive list of polypeptide molecules that include, or could be modified to include, an N-terminal cysteine or histidine residue: calcitonin, parathyroid hormone, interferon alpha, interferon beta, interferon gamma, interleukins 1-21, granulocyte-colony stimulating factor, macrophage-colony stimulating factor, granulocyte-macrophage colony stimulating factor, stem cell factor, leukemia inhibitory factor, kit-ligand, flt-3 ligand, erythropoietin, thrombopoietin, tumor necrosis factor alpha, tumor necrosis factor beta, transforming growth factor, bone morphogenic proteins, osteoprotegerin, tissue plasminogen activator, platelet derived growth factor, fibroblast growth factor, keratinocyte growth factor, epidermal growth factor, human growth hormone, insulin, tumor necrosis factor-related apoptosis-inducing ligand (TRAIL), DNAse, receptors, enzymes, fusion proteins, chimeric antibodies, humanized antibodies, fully human antibodies, Fab fragments, F(ab')$_2$ fragments, Fv fragments, and scFv fragments. In one preferred embodiment, the polypeptide is an interferon molecule.

An exemplary embodiment of a linear polymer conjugate of the invention has the structure:

Formula VIIa

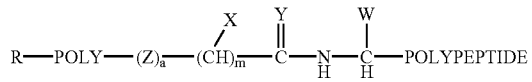

wherein R, POLY, Z, a, X, m, Y and W are as defined above.

In an alternative embodiment where the polymer is a multi-arm polymer, an exemplary polymer conjugate of the invention has the structure:

is preferably effected by use of a trialkylphosphine, such as tris(2-carboxyethyl)phosphine or triethylphosphine, and optionally a thiol, such as mercaptopropionic acid.

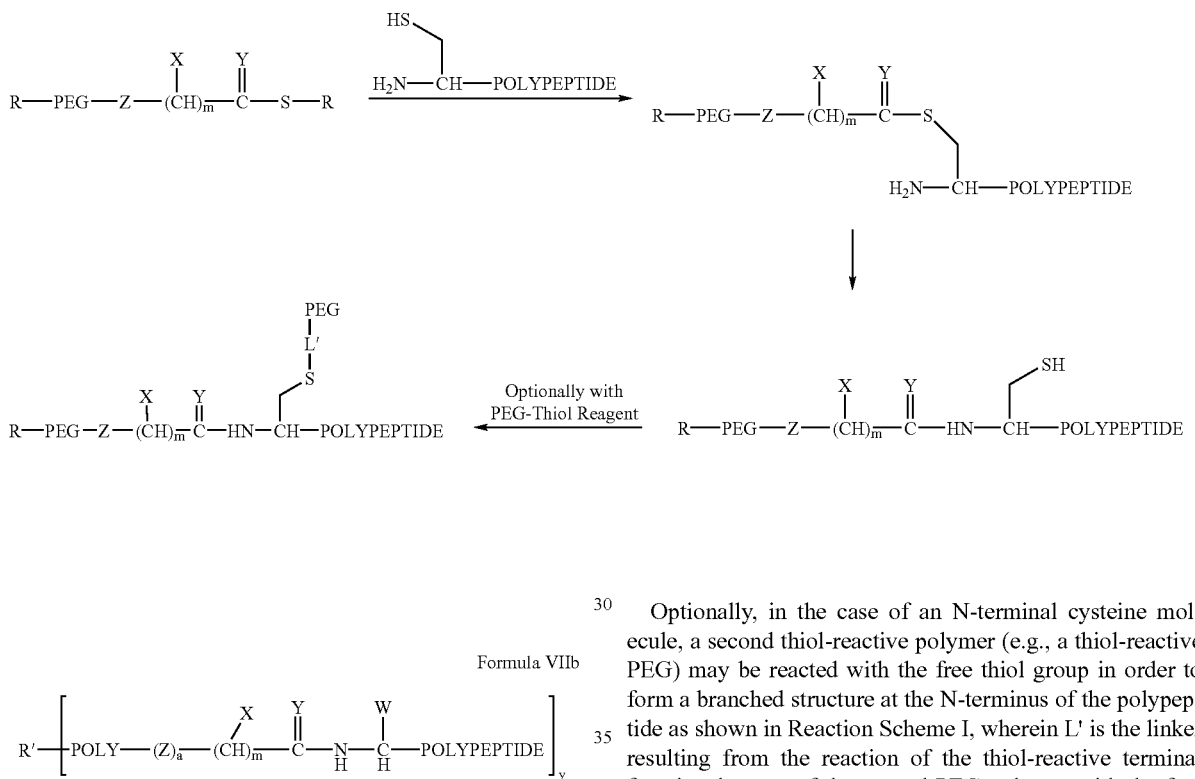

Reaction Scheme I

Formula VIIb wherein R', y, POLY, Z, a, X, m, Y and W are as defined above.

Polypeptide conjugates in accordance with the invention will possess an amide linkage formed by reaction with an N-terminal cysteine or histidine of the polypeptide, where the polymer portion of the conjugate may have any of a number of different geometries (e.g., linear, branched, forked, and the like), molecular weights, optional degradable linkages, etc., as described in detail herein and in the accompanying examples. Representative conjugates prepared in accordance with the invention are provided in Examples 4–7.

B. Method of Forming Polymer/Polypeptide Conjugate

The present invention uses a thioester-terminated polymer, such as a thioester-terminated PEG, to specifically modify the a-amine of an N-terminal cysteine or histidine without permanently modifying the remaining free functional group (e.g., the thiol group of a cysteine residue) on the terminal amino acid or modifying other amine groups present in the polypeptide chain. Although not bound by any particular theory, Reaction Scheme I below illustrates the reaction believed to occur between a polypeptide having an N-terminal cysteine molecule and a reactive polymer of the invention. As shown, it is believed that the thioester-terminated polymer initially reacts with the free thiol group of the cysteine and thereafter undergoes an intramolecular rearrangement to form an amide linkage with the N-terminal amine group, thus leaving the thiol group available for further modification if desired. The thiol-thioester exchange Optionally, in the case of an N-terminal cysteine molecule, a second thiol-reactive polymer (e.g., a thiol-reactive PEG) may be reacted with the free thiol group in order to form a branched structure at the N-terminus of the polypeptide as shown in Reaction Scheme I, wherein L' is the linker resulting from the reaction of the thiol-reactive terminal functional group of the second PEG polymer with the free thiol group on the cysteine molecule. In one embodiment, only two polymer backbones are attached to the polypeptide.

Examples of thiol-reactive functional groups include vinylsulfone, maleimide, orthopyridyl disulfide and iodoacetamide. Examples of the L' linkage include:

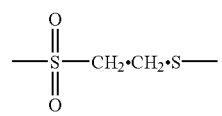

(resulting from vinylsulfone functional group)

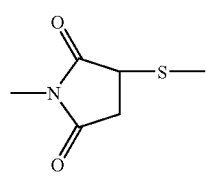

(resulting from maleimide functional group)

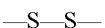

(resulting from orthopyridyl disulfide functional group)

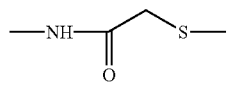

(resulting from iodoacetamide functional group)

As would be readily understood by one of ordinary skill in the art, the method of the invention could be used to couple the above-described polymer derivatives to any moiety, whether peptidic or not, having a terminal —CH(W)—NH$_2$ group, wherein W is as defined above.

IV. EXAMPLES

The following examples are given to illustrate the invention, but should not be considered in limitation of the invention. For example, although MPEG is used in the examples to illustrate the invention, other forms of PEG and similar polymers that are useful in the practice of the invention are encompassed by the invention as discussed above.

All PEG reagents referred to in the appended examples are available from Shearwater Corporation of Huntsville, Ala. All $^+$HNMR data was generated by a 300 or 400 MHz NMR spectrometer manufactured by Bruker.

Examples 1–3 illustrate methods of forming a thioester-terminated polymer of the invention. Examples 4–7 illustrate reaction of a thioester-terminated polymer of the invention with an exemplary polypeptide having a N-terminal cysteine residue. As indicated below, use of the thioester polymers of the invention results in selective attachment of the polymer to the N-terminal amine of the polypeptide.

Example 1

Preparation of PEG(5000)-α-methoxy-ω-propionic Acid, 2-pyridylthioester (PEG-PA-OPTE)

CH$_3$O—CH$_2$CH$_2$(OCH$_2$CH$_2$)$_\overline{n}$—O—(CH$_2$)$_2$—C(=O)—S—(pyridyl)

2-mercaptopyridine (40.0 mg, 0.36 mmoles), 1-hydroxybenzotriazole (4.0 mg, 0.030 mmoles), 4-(dimethylamino)pyridine (36.7 mg, 0.30 mmoles) and 1,3-dicyclohexylcarbodiimide (dissolved in 2 mL anhydrous dichloromethane, 84.0 mg, 0.41 mmoles) were added to a solution of PEG (5000)-α-methoxy-ω-propionic acid (1.5 g, 0.27 mmoles) in anhydrous acetonitrile (20 mL). The reaction solution was stirred overnight at ambient temperature under argon. The solution was then concentrated to near dryness at reduced pressure, followed by addition of anhydrous toluene (50 mL). The mixture was stirred at room temperature for thirty minutes, filtered and the filtrate was concentrated at reduced pressure to near dryness. Ethyl acetate (200 mL) was added and the mixture was warmed until the contents were completely dissolved. The solution was then cooled to room temperature while stirring. Ethyl ether (50 mL) was added and a precipitate formed. The product was filtered and rinsed with ethyl ether until the product became white. The product was then dried under high vacuum. Yield: 1.1 g. NMR (d6-DMSO): δ2.98 ppm (t, 2H, —CH$_2$—COS—), δ3.51 ppm (s, PEG backbone), δ7.46 ppm (m, ill resolved, 1H, H$_5$ (pyridyl)), δ6.64 ppm (d, 1H, H$_3$ (pyridyl)), δ7.91 ppm (t, 1H, H$_4$ (pyridyl)), δ8.60 ppm (d, 1H, H$_6$ (pyridyl)).

Example 2

Preparation of PEG(5000)-α-benzyloxy(BZO)-ω-carboxymethyl, 2-pyridylthioester (PEG-CM-OPTE)

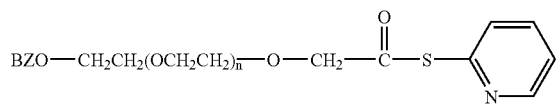

2-mercaptopyridine (40.0 mg, 0.36 mmoles), 1-hydroxybenzotriazole (5.0 mg, 0.035 mmoles), and 1,3-dicyclohexylcarbodiimide (dissolved in 2 mL anhydrous dichloromethane, 74.3 mg, 0.36 mmoles) were added to a solution of PEG(5000)-α-benzyloxy-ω-carboxymethyl (1.5 g, 0.30 mmoles) in anhydrous acetonitrile (20 mL). The reaction solution was stirred overnight at ambient temperature under argon. The solution was then concentrated to near dryness at reduced pressure, followed by addition of anhydrous toluene (30 mL). The mixture was stirred at room temperature for thirty minutes, filtered and the filtrate was concentrated at reduced pressure to near dryness. Ethyl acetate (150 mL) was added and the mixture was warmed until the contents were completely dissolved. The solution was then cooled to room temperature while stirring. Ethyl ether (50 mL) was added to the solution and a precipitate formed. The product was filtered and rinsed with ethyl ether until the product became white. The product was then dried under high vacuum. Yield: 1.1 g. NMR (d6-DMSO): δ3.51 ppm (s, PEG backbone), δ4.39 ppm (s, 2H, —OCH$_2$COS—), δ4.49 ppm (s, 2H, —OCH$_2$-(benzyloxy)), δ7.33 ppm (m, ill resolved, 5H, C$_6$H$_5$ (benzyloxy)), δ7.46 ppm (m, ill resolved, 1H, H$_5$ (pyridyl)), δ7.63 ppm (d, 1H, H$_3$ (pyridyl)), δ7.91 ppm (t, 1H, H$_4$ (pyridyl)), δ8.60 ppm (d, 1H, H$_6$ (pyridyl)).

Example 3

Preparation of PEG(5000)-α-methoxy-ω-2-methyl butanoic acid, 2-pyridylthioester

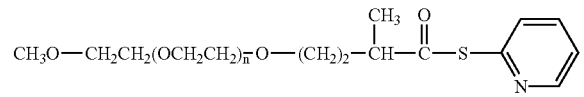

2-mercaptopyridine (44.5 mg, 0.40 mmoles), 1-hydroxybenzotriazole (4.7 mg, 0.033 mmoles), 4-(dimethylamino)pyridine (40.7 mg, 0.33 mmoles) and 1,3-dicyclohexylcarbodiimide (dissolved in 2 mL anhydrous dichloromethane, 92.8 mg, 0.45 mmoles) were added to a solution of PEG (5000)-α-methoxy-ω-2-methyl butanoic acid (1.5 g, 0.30 mmoles) in anhydrous acetonitrile (20 mL). The reaction solution was stirred overnight at ambient temperature under argon. The solution was then concentrated to near dryness at reduced pressure, followed by addition of anhydrous toluene (50 mL). The mixture was stirred at room temperature for thirty minutes, filtered and the filtrate was concentrated at reduced pressure to near dryness. Ethyl acetate (150 mL) was added and mixture was warmed until the contents completely dissolved. The solution was then cooled to room temperature while stirring. A precipitate was formed by adding 2-Propanol (50 mL), followed by addition of ethyl ether (50 mL). The product was filtered off, rinsed with 2-propanol until the product became white. The product was then dried under high vacuum. Yield: 1.2 g. NMR (d6-DMSO): $\delta$1.19 ppm (d, 3H, —O—CH$_2$—CH$_2$—CH(CH$_3$)—COS—), $\delta$1.66 ppm and $\delta$1.92 ppm (mm, 2H, —O—CH$_2$—CH$_2$—CH(CH$_3$)—$\delta$2.89 ppm (m, 1H, —O—CH$_2$—CH$_2$—CH(CH$_3$)—COS—), $\delta$3.51 ppm (s, PEG backbone), $\delta$7.46 ppm (m, ill resolved, 1H, H$_5$ (pyridyl)), $\delta$7.63 ppm (d, 1H, H$_3$ (pyridyl)), $\delta$7.90 ppm (t, 1H, H$_4$ (pyridyl)), $\delta$8.60 ppm (d, 1H, H$_6$ (pyridyl)).

Example 4

Conjugation of PEG-CM-OPTE to Interferon

Interferon tau (0.45 mg), which has a cysteine as the N-terminal amino acid, was formulated to 0.3 mg/ml in 1M Tris, 0.7 mM TCEP (Tris[2-carboxyethylphosphine]hydrochloride) and 3 mM mercaptopropionic acid at pH 7.75. Approximately 1.0 mg of mPEG$_{5K}$-CM-OPTE (from Example 2) was added to the interferon solution and allowed to react at room temperature for 4 hours. The reaction mixture was dialyzed against deionized water overnight. The product was analyzed by MALDI-MS. The mass spectrum showed free PEG at 5000 Da, unconjugated interferon at 19,979 Da and a single PEG conjugate at a molecular weight of 25,065 Da, meaning the PEGylated product has only a single PEG molecule attached to the polypeptide at the N-terminus.

Example 5

Conjugation of PEG-PA-OPTE to Interferon

Interferon tau (0.45 mg) was formulated to 0.3 mg/ml in 0.33M Tris, 0.7 mM TCEP (Tris[2-carboxyethylphosphine]hydrochloride) at pH 7.75. Approximately 1.0 mg of mPEG$_{5K}$-PA-OPTE (orthopyridyl thioester of propionic acid from Example 1) was added to the interferon solution and allowed to react at room temperature for 4 hours. The product was analyzed by SDS-PAGE. The gel showed two bands corresponding to unconjugated interferon (~20 kDa) and singly PEG-conjugated interferon (~29 kDa) (i.e., a polypeptide attached to a single PEG molecule). The slower migration of the PEG-interferon conjugate is due to the larger hydrodynamic volume of the PEG chain when compared to a corresponding molecular weight protein.

Example 6

Conjugation of PEG-CM-OPTE to a Polypeptide

The polypeptide CRASKSVSSSGYSYMHWYQQ (MW=2355 Da) (SEQ ID NO: 1) was formulated to 0.67 mg/ml in 0.67M Tris, 1.3 mM TCEP (Tris[2-carboxyethylphosphine]hydrochloride) and 5.3M urea at pH 7.75. Approximately 21.0 mg of mPEG$_5$K-CM-OPTE (from Example 2) was added to the polypeptide solution and allowed to react at room temperature for 4 hours. The reaction mixture was dialyzed against deionized water overnight. The product was analyzed by MALDI-MS. The mass spectrum showed a conjugate comprising a single PEG molecule attached to the polypeptide and having a molecular weight of 7555 Da. This demonstrates that the thioester-terminated polymer did not randomly react with other free amine groups in the molecule, such as the amine groups of the lysine or arginine residues.

Example 7

Conjugation of PEG-PA-OPTE to a Polypeptide

The polypeptide CRASKSVSSSGYSYMHWYQQ (MW=2355 Da) (SEQ ID NO: 1) was formulated to 0.67 mg/ml in 0.67M Tris, 1.3 mM TCEP (Tris[2-carboxyethylphosphine]hydrochloride) and 5.3M urea at pH 7.75. Approximately 21.0 mg of mPEG$_5$K-PA-OPTE (from Example 1) was added to the polypeptide solution and allowed to react at room temperature for 4 hours.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A polymer conjugate of a polypeptide having a cysteine or histidine residue at the N-terminus, said polymer conjugate comprising a water salable and non-peptidic polymer backbone having at least one terrminus bonded to the structure:

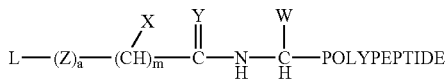

wherein:
L is the paint of bonding to the polymer backbone;
Z is a linker;
Y is a heteroatom;
m is from 0 to about 12;
each X is independently selected from H and alkyl;
a is 0 or 1;
W is —CH$_2$SH or

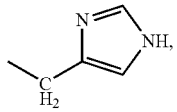

and
POLYPEPTIDE is a residue of the polypeptide molecule.

2. The polymer conjugate of claim 1, wherein the polymer backbone is poly(ethylcne glycal).

3. The polymer conjugate of claim 1, wherein POLYPEPTIDE is a residue of a polypeptide selected from the group consisting of proteins, protein-ligands, enzymes, cytolcines, hematopoietins, growth factors, hormones, antigens, antibodies, antibody fragments, receptors, and protein fragments.

4. The polymer conjugate of claim 1, wherein POLYPEPTIDE is a residue of an interferon molecule.

5. A method of conjugating a polymer derivative to a polypeptide having a cysteine or histidine residue at the N-terminus, said method comprising:
providing a polypeptide having a cysteine or histidine residue at the N-terminus,
providing a thioester-terminated polymer, the polymer comprising a water soluble and non-peptide polymer backbone having at least one terminus bonded to the structure:

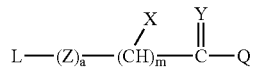

wherein:
L is the point of bonding to the polymer backbone;
Z is a linker;
m is from 0 to about 12;
Y is a heteroatom;
each X is independently selected from H and alkyl;
a is 0 or 1; and
Q is a sulfur-containing leaving group;
reacting the thioester-terminated polymer with the polypeptide to form a conjugate having the structure:

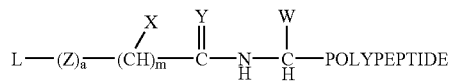

wherein
POLYPEPTIDE is a residue of the polypeptide molecule, and

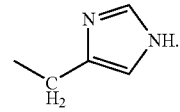

6. The method of claim 5, wherein the polymer backbone is poly(ethylene glycol).

7. The method of claim 5, wherein POLYPEPTIDE is a residue of a polypeptide selected from the group consisting of protein ligands, enzymes, cytokines, hematopoietins, growth factors, hormones, antigens, antibodies, antibody fragments, receptors, and protein fragments.

8. A polymer conjugate of a polypeptide having a cysteine molecule at the N-terminus, said polymer conjugate comprising two water soluble and non-peptidic polymer backbones attached at the N-terminus, the conjugate having the structure:

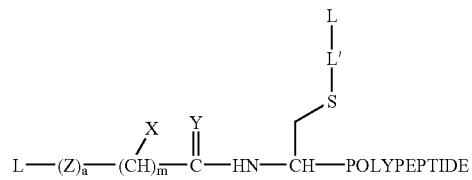

wherein:
L is the point of bonding to each of said two polymer backbones,
L' and Z are linkers,
Y is a heteroatom;
m is from 0 to about 12;
each X is independently selected from H and alkyl;
a is 0 or 1; and
POLYPEPTIDE is a residue of the polypeptide molecule.

9. The polymer conjugate of claim 8, wherein L' is selected from the group consisting of

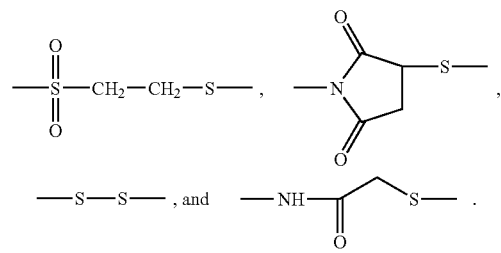

10. The polymer conjugate of claim 1, wherein each X is H or Cl–C6 alkyl.

11. The polymer conjugate of claim 10, wherein each X is H or methyl.

12. The polymer conjagate of claim 1, wherein Y is O or S.

13. The polymer conjugate of claim 1, wherein a is 1 and Z is selected from the group consisting of —O—, —S—, —NHCO—, —CONH—, —O$_2$C—, —NHCO$_2$—, and —O$_2$CNH—.

14. The polymer conjugate of claim 1, wherein the polymer backbone is selected from the group consisting of poly(alkylene glycol), poly(oxyethylated potyol), poly(olefinic alcohol), poly(vinylpyrrolidone), poly(α-hydroxy acid), poly(vinyl alcohol), polyphosphazene, polyoxazoline, poly(N-acryloylmorpholinc), polyacrylate, polyacrylamides, polysaecharides, and copolymers, terpolymers, and mixtures thereof.

15. The polymer conjugate of claim 1, wherein the polymer backbone is selected from the group consisting of poly(ethylene glycol, poly(propylene glycol), and copolymers of ethylene glycol and propylene glycol.

16. The polymer conjugate of claim 1, wherein the polymer backbone is poly(erhylene glycol) having a number average molecular weight of about 100 Da to about 100,000 Da.

17. The polymer conjugate of claim 16, wherein the poly(ethylene glycol) has a number average molecular weight of about 2,000 Da to about 60,000 DL.

18. The polymer conjugate of claim 16, wherein the poly(ethylene glycol) has the formula —CH$_2$CH$_2$O—(CH$_2$CH$_2$O)$_{11}$—CH$_2$CH$_2$—, wherein n is from about 1 to about 2000.

19. The polymer conjugate of claim 1, wherein m is 1 to about 4.

20. The polymer conjugate of claim 1, having the structure:

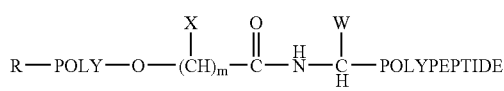

wherein
R is methoxy;
POLY is poly(ethylene glycol) having a number average molecular weight of about 2,000 Da to about 60,000 Da;
each X is H or CH$_3$;
m is 1 to about 4;
W is —CH$_2$SH or

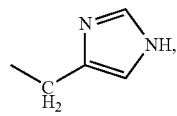

and
POLYPEPTIDE is a residue of the polypeptide molecule.

21. The polymer conjugate of claim 20, wherein X is H and m is 1.

22. The polymer conjugate of claim 20, wherein each X is H and m is 2.

23. The polymer conjugate of claim 20, wherein —(CH(X))$_m$—has the structure —CH$_2$—CH$_2$—CH(CH$_3$)—.

24. The method of claim 5, wherein Q has the formula —S-R$_1$, wherein R$_1$ is selected from the group consisting of hydrogen, alkyl, substituted alkyl, cycloalkyl, substituted cycloalkyl, aryl, substituted aryl, heteroaryl, substituted heteroaryl, heterocycle, and substituted hetorocycle.

25. The method of claim 24, wherein R$_1$ is selected from the group consisting of phenol, nitrophenol, beazoic acid, pyridine, pyridinecarboxylic acid, and nitropyridine.

26. The method of claim 24, wherein R$_1$ is substituted or unsubstituted pyridine.

27. The method of claim 5, wherein a is 1 and Z is selected from the group consisting of —O—, —S—, —NHCO—, —CONH—, —O$_2$C—, —NHCO$_2$—, and —O$_2$CNH—.

28. The method of claim 5, wherein the polymer backbone is selected from the group consisting of paly(alkylene glycol), poly(oxyethylated polyol), poly(olefinic alcohol), poly(vinylpyrrolidone), poly(α-hydroxy acid), poly(vinyl alcohol), polyphosphazene. polyoxazoline, poly(N-acryloylmorpholine), polyacrylate, polyacrylamides, polysaccharides, and copolymers, terpolymers, and mixtures thereof.

29. The method of claim 5, wherein the polymer backbone is selected from the group consisting of poly(ethylene glycol), poly(propylene glycol), and copolymers of ethylene glycol and propylene glycol.

30. The method of claim 5, wherein the polymer backbone is poly(ethylene glycol) having a number average molecular weight of about 100 Da to about 100,000 Da.

31. The method of claim 5, wherein m is 1 to about 4.

32. The method of claim 5, wherein the thioester-terminated polymer has the structure:

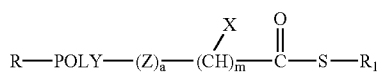

wherein:
POLY is a water soluble and non-peptidic polymer backbone;
R$_1$ is a capping group or a functional group; and
R$_1$ is selected from the group consisling of hydrogen, alkyl, substituted alkyl, cycloalkyl, substiuted cycloalkyl, aryl, substituted aryl, heteroaryl, substituted heteroaryl, heterocycle, and substituted heterocycle.

33. The method of claim 32, wherein R is selected from the group consisting of alkoxy, alkyl, benzyl, aryl, aryloxy, hydroxyl, active ester, active carbonate, acetal, aldehyde, aldehyde hydrate, alkenyl, acrylate, methacrylate, acrylamide, active sulfone, amine, hydraizide, thiol, carboxylic acid, isocyanate, isorhiocyanate, maleimide, vinylsulfone, dithiopyridine, vinylpyridine, iodoacctamide, epoxide, glyoxal, dione, mesylate, tosylate, tresylate and -(Z)$_u$—(CXH)$_m$—CO—S-R$_1$.

34. The method of claim 32, wherein R is methoxy.

35. The method of claim 32, wherein POLY is poly(ethylene glycol).

36. The method of claim 32, wherein the tbioester-terminated polymer has a structure selected from the group consisting of

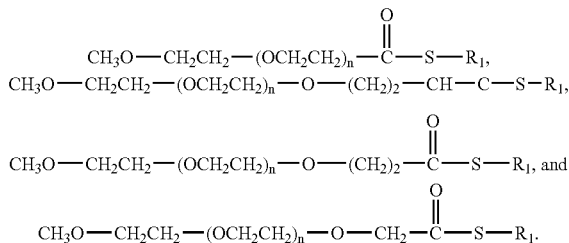

wherein n is from about 20 to about 2,000.

37. The method of claim 32, wherein the thioester-terminated polymer has the structure:

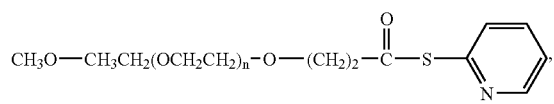

wherein n is from about 20 to about 2,000.

38. The method claim 32, wherein the thioester-terminated polymer has the structure:

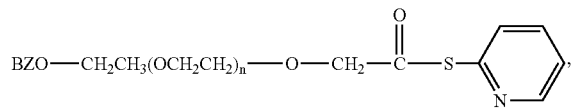

wherein BZ is benzyl and n is from about 20 to about 2,000.

39. The method of claim 32, wherein the thioester-terminated polymer has the structure:

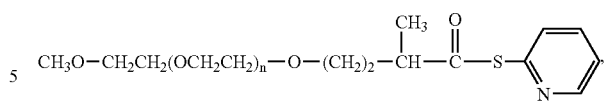

wherein n is from about 20 to about 2,000.

40. The method of claim 5, wherein the thioester-terminated polymer has the structure:

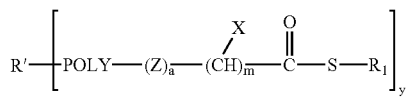

wherein:
- each POLY is a water soluble and non-peptidic polymer backbone;
- R' is a central core molecule;
- y is from about 3 to about 100: and
- $R_1$ is selected from the group consisting of hydrogen, alkyl, substituted alkyl, cycloalkyl, substituted cycloalkyl, aryl, substituted aryl, hetoroaryl, substituted heteroaryl, heterocycle, and substituted heterocycle.

41. The method of claim 40, wherein POLY is poly (cthylene glycol).

42. The method of claim 40, wherein R' is a residue of a molecule selected from the group consisting of polyols, polyamines, and molecules having a combination of alcohol and amine groups.

43. The method of claim 40, wherein R' is a residue of a molecule selected from the group consisting of glycerol, glycerol oligomers, pentaerythritol, sorhitol, and lysine.

* * * * *

UNITED STATES PATENT AND TRADEMARK OFFICE
CERTIFICATE OF CORRECTION

PATENT NO. : 7,078,496 B2
APPLICATION NO. : 10/269028
DATED : July 18, 2006
INVENTOR(S) : Roberts et al.

It is certified that error appears in the above-identified patent and that said Letters Patent is hereby corrected as shown below:

Column 23,

Line 4, "salable" should read --soluble--;

Line 14, "paint" should read --point--;

Line 33, "poly(ethylcne glycal)" should read -- poly(ethylene glycol)--;

Line 36, "cytolcines" should read --cytokines--.

Column 24,

Line 10, before the formula, insert --W is -$CH_2SH$ or--.

Column 25,

Line 1, "conjagate" should read --conjugate--;

Line 9, "potyol" should read --polyol--;

Line 12, "N-acryloylmorpholinc" should read --N-acryloylmorpholine--;

Line 13, "polysaecharides" should read --polysaccharides--;

Line 22, "erhylene" should read --ethylene--;

Line 27, "DL" should read --Da--;

Line 30, "$(CH_2CH_2O)_{11}$" should read --$(CH_2CH_2O)_n$--.

Column 26,

Line 7, "beazoic" should read --benzoic--;

Lines 17-18, "paly(alkylene glycol)" should read --poly(alkylene glycol)--;

Line 20, "polyphosphazene." should read --polyphosphazene,--;

Line 46, "$R_1$ is a capping group" should read --R is a capping group--;

Line 47, "consisling" should read --consisting--;

Line 55, "hydraizide" should read --hydrazide--;

Line 56, "isorhiocyanate" should read --isothiocyanate--;

UNITED STATES PATENT AND TRADEMARK OFFICE
CERTIFICATE OF CORRECTION

PATENT NO. : 7,078,496 B2
APPLICATION NO. : 10/269028
DATED : July 18, 2006
INVENTOR(S) : Roberts et al.

It is certified that error appears in the above-identified patent and that said Letters Patent is hereby corrected as shown below:

Column 26 cont'd

Line 57, "iodoacctamide" should read --iodoacetamide--;

Line 58, "$(Z)_u$" should read --$(Z)_a$--;

Line 64, "tbioester" should read --thioester--.

Column 27,
Line 5,

""

should read

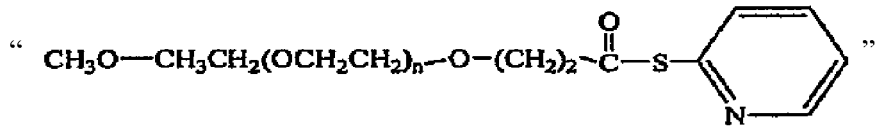

Line 20,

"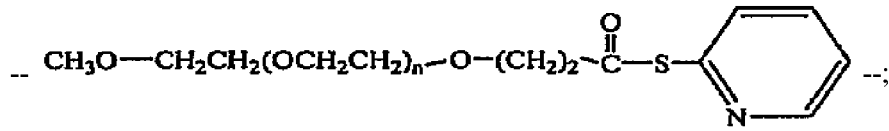"

should read

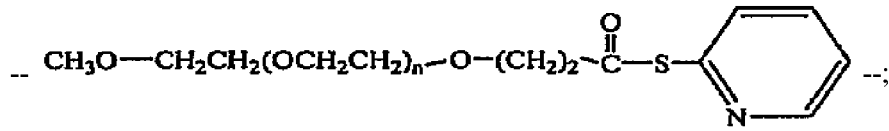

UNITED STATES PATENT AND TRADEMARK OFFICE
CERTIFICATE OF CORRECTION

PATENT NO. : 7,078,496 B2  Page 3 of 3
APPLICATION NO. : 10/269028
DATED : July 18, 2006
INVENTOR(S) : Roberts et al.

It is certified that error appears in the above-identified patent and that said Letters Patent is hereby corrected as shown below:

Line 31,

" 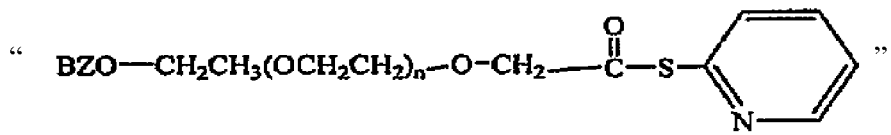 "

should read

-- 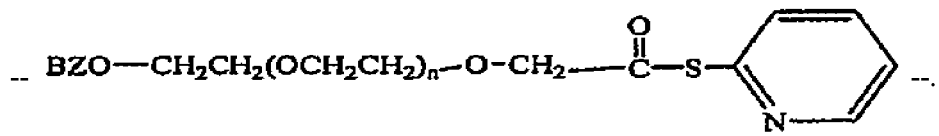 --.

Column 28,

Line 29, "cthylene" should read --ethylene--.

Signed and Sealed this

Twenty-sixth Day of December, 2006

JON W. DUDAS
*Director of the United States Patent and Trademark Office*